(12) United States Patent
Jay et al.

(10) Patent No.: US 8,030,358 B2
(45) Date of Patent: Oct. 4, 2011

(54) METHODS AND PHARMACEUTICAL COMPOSITIONS FOR DECORPORATION OF RADIOACTIVE COMPOUNDS

(75) Inventors: Michael Jay, Chapel Hill, NC (US); Russell J. Mumper, Chapel Hill, NC (US)

(73) Assignee: University of Kentucky Research Foundation, Lexington, KY (US)

( * ) Notice: Subject to any disclaimer, the term of this patent is extended or adjusted under 35 U.S.C. 154(b) by 532 days.

(21) Appl. No.: 12/260,549

(22) Filed: Oct. 29, 2008

(65) Prior Publication Data

US 2009/0124692 A1   May 14, 2009

Related U.S. Application Data

(60) Provisional application No. 60/983,401, filed on Oct. 29, 2007.

(51) Int. Cl.
*A61K 31/13* (2006.01)
(52) U.S. Cl. .......................... 514/663; 514/667; 514/668
(58) Field of Classification Search .................. 514/663, 514/667, 668
See application file for complete search history.

(56) References Cited

U.S. PATENT DOCUMENTS

| | | | |
|---|---|---|---|
| 4,687,659 | A | 8/1987 | Quay |
| 4,780,238 | A | 10/1988 | Premuzic |
| 4,859,451 | A | 8/1989 | Quay et al. |
| 5,250,702 | A | 10/1993 | Kondo et al. |
| 5,288,718 | A | 2/1994 | Varga et al. |
| 5,403,862 | A | 4/1995 | Miller et al. |
| 5,440,031 | A | 8/1995 | Varga et al. |
| 5,494,935 | A | 2/1996 | Miller et al. |
| 5,780,670 | A | 7/1998 | Yamamoto et al. |
| 6,020,373 | A | 2/2000 | Schellenberg et al. |
| 6,060,040 | A | 5/2000 | Tournier et al. |
| 6,241,968 | B1 | 6/2001 | Tournier et al. |
| 2007/0196273 | A1 | 8/2007 | Shankar et al. |

OTHER PUBLICATIONS

U.S. Food and Drug Administration, FDA News, FDA Approves Drugs to Treat Internal Contamination from Radioactive Elements, Aug. 11, 2004, www.fda.gov/bbs/topics/news/2004/NEW01103.html.
Depatment of Health and Human Services, CDC Fact Sheet, Diethylenetriamene pentaacetate (DTPA), Oct. 11, 2006.
Radiation Event Medical Management, Ca-DTPA/Zn-DTPA (Diethylentriamene pentaacetate), Jul. 25, 2007, www.remm.nlm.gov/dtpa.htm.

*Primary Examiner* — Raymond Henley, III
(74) *Attorney, Agent, or Firm* — King & Schickli, PLLC

(57) ABSTRACT

A composition for removing a radioactive element or compound such as systemic transuranic compounds, from mammals comprises a pharmaceutical carrier and a decorporation agent comprising ester and amide derivatives of DTPA. A method of treating a mammal to remove systemic compounds utilizing the DTPA derivatives is also disclosed.

21 Claims, 2 Drawing Sheets

METHODS AND PHARMACEUTICAL COMPOSITIONS FOR DECORPORATION OF RADIOACTIVE COMPOUNDS

This application claims the benefit of U.S. provisional patent application Ser. No. 60/983,401 filed on 29 Oct. 2007.

This invention was made with at least partial Government support under National Institutes of Health Award No. HHSN266200500045C. The Government may have certain rights in this invention.

TECHNICAL FIELD

The present invention relates generally to chelating agents and to related methods for utilizing those chelating agents in pharmaceutical compositions to decorporate or remove transuranic or other radioactive elements and compounds, from mammals such as humans.

BACKGROUND OF THE INVENTION

The calcium and zinc salts of diethylenetriamine pentaacetate (Ca-DTPA and Zn-DTPA) have been approved by the Food and Drug Administration for the decorporation, removal or elimination of known or suspected internal contamination of humans with the transuranic metals (Z>92), plutonium, americium and curium. More specifically Ca-DTPA and Zn-DTPA are chelating agents that work by binding and holding onto radioactive materials or certain other poisons that enter the body. Once bound to the radioactive material or poison, the chelating agent is then passed from the body in the urine and or feces. The chelating agents help decrease the amount of time it takes to get the poison out of the body.

Ca-DTPA and Zn-DTPA are not absorbed from the GI tract to any appreciable extent and therefore must be administered by (1) subcutaneous injection directly into a vein, (2) intravenously by dripping into a vein from a bag or (3) by nebulized inhalation by means of a mist or spray breathed into the lungs.

A need exists for the development of a form of diethylene triamine penta-acetic acid (DTPA) that can be administered orally for use in the possible event of a massive radiation poisoning emergency such as could occur by the detonation of a dirty bomb by terrorists or inadvertent release of radioactivity into a work place or the environment. The present invention relates to pharmaceutical compositions and treatment methods meeting this need. More specifically, esters and amides of DTPA have been developed that are readily absorbed following oral administration and are subsequently and rapidly hydrolyzed back to active DTPA by esterases or amidases normally present in the intestinal lumen, liver and/ or blood.

SUMMARY OF THE INVENTION

In accordance with the purposes of the present invention as described herein, a method is provided for treating a mammal to remove systemic transuranic or other radioactive elements and compounds. The method is broadly described as comprising the step of administrating to the mammal a pharmaceutically effective amount of a decorporation agent having a chemical formula

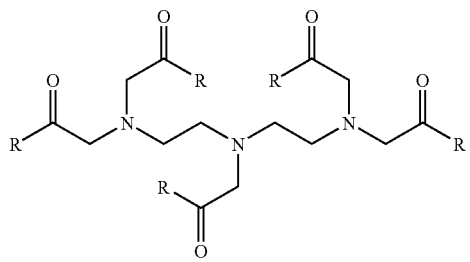

where R=—OR$^1$ or —NHR$^2$;
R$^1$=same or different and is independently selected from H, $C_1$-$C_{30}$ alkyl, $C_2$-$C_{30}$ alkenyl, $C_2$-$C_{30}$ alkynyl or benzyl and at least one R$^1$ is not hydrogen; and
R$^2$=same or different and is independently selected from $C_1$-$C_{30}$ alkyl, $C_2$-$C_{30}$ alkenyl, $C_2$-$C_{30}$ alkynyl, benzyl or phenylalanine ethyl ester.

More specifically describing the invention, the method includes administering preferably between about 5 and about 250 milligrams of decorporation agent per kilogram of the total weight of the mammal per day. More preferably, the dose is between 5 to 100 milligrams/kg body weight, and most preferably the dose is between 15 to 45 milligrams/kg body weight.

The method may further include administering the decorporation agent for an extended period of time such as over days and weeks in order to achieve medically sufficient decorporation.

In accordance with an additional aspect of the present invention a method is provided for treating a mammal to remove radioactive elements and compounds comprising the step of administering to the mammal a pharmaceutically effective amount of a pharmaceutical composition including a pharmaceutical carrier and a decorporation agent having a chemical formula

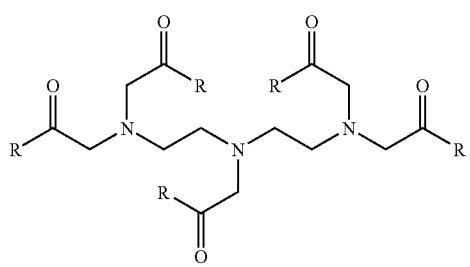

where R=—OR$^1$ or —NHR$^2$;
R$^1$=same or different and is independently selected from H, $C_1$-$C_{30}$ alkyl, $C_2$-$C_{30}$ alkenyl, $C_2$-$C_{30}$ alkynyl or benzyl and at least one R$^1$ is not hydrogen; and
R$^2$=same or different and is independently selected from $C_1$-$C_{30}$ alkyl, $C_2$-$C_{30}$ alkenyl, $C_2$-$C_{30}$ alkynyl, benzyl or phenylalanine ethyl ester.

The pharmaceutical composition may further include an antioxidant, a preservative and/or a binder, a viscosity enhancing agent, and a sweetening agent as desired depending upon the form of the product (eg. liquid dosage forms and solid dosage forms such as powder, pill, tablet, capsule, gel cap for oral administration).

In accordance with yet another aspect of the present invention a composition is provided for removing systemic radioactive compounds from a mammal. The composition comprises a pharmaceutical carrier and a pharmaceutically effective amount of a decorporation agent having a chemical formula

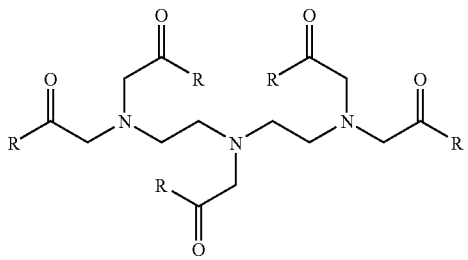

where R=—OR$^1$ or —NHR$^2$;

R$^1$=same or different and is independently selected from H, $C_1$-$C_{30}$ alkyl, $C_2$-$C_{30}$ alkenyl, $C_2$-$C_{30}$ alkynyl or benzyl and at least one R$^1$ is not hydrogen; and R$^2$=same or different and is independently selected from $C_1$-$C_{30}$ alkyl, $C_2$-$C_{30}$ alkenyl, $C_2$-$C_{30}$ alkynyl, benzyl or phenylalanine ethyl ester.

For oral administration, the carrier may be a solution comprised of a mixture of solvents including, but not limited to, water, ethanol, propylene glycol, glycerin, cornoil, ethyl oleate, glycofurol, mineral oil, peanut oil, polyethylene glycol, propylene glycol, sesame oil, soybean oil, or triacetin. The viscosity of the vehicle can also be increased with any number of agents including, but not limited to, acacia, alcohols, alginic acid, carbomer, carboxymethylcellulose, ethylcellulose, povidone, or xanthum gum. The pH of the vehicle can also be adjusted to a pH that best stabilizes the decorporation agent. The preferred pH is in the range of pH 2-8 while the pH range of 3-7.5 is more preferred, and the pH range of 3.5 to 7 is most preferred. pH adjusting agents include, but are not limited to, citric acid/citrate, phosphoric acid/phosphate, or boric acid/borate.

The composition for an oral solution includes between about 50 and about 98 weight percent pharmaceutical carrier with the decorporation agent in the pharmaceutical carrier at a concentration ranging from 5 to 250 mg/mL, and more preferably at a concentration ranging from 50 to 150 mg/mL.

The composition may further include between 0.001 and about 3 weight percent antioxidant. The antioxidant may be selected from a group consisting of ascorbic acid, its salts and esters; fumaric acid, its salts and esters; malic acid, its salt and esters; alpha-tocopherol, its salts and esters; sodium metabisulphite, sodium bisulfite; butylated hydroxyanisole (BHA); butylated hydroxytoluene (BHT); gallic acid, its salts and esters; EDTA. It is well known that other compounds not listed can have antioxidant properties and these compounds are not intentionally omitted herein.

The composition may further include between about 0.001 and about 10 weight percent preservative. That preservative may be selected from a group consisting of methylparaben, ethylparaben, propylparaben, butylparaben, benzoic acid, sodium benzoate, benzyl alcohol, sorbic acid and potassium sorbate, EDTA, glycerol, phenol, thimerosol, phenoxyethanol, and cresol. It is well known that other compounds not listed can have preservative properties and these compounds are not intentionally omitted herein.

Further the composition may include between about 0.01 and about 25 weight percent binder. The binder may be selected from a group consisting of microcrystalline cellulose, silicon dioxide, dibasic calcium phosphate, starch, glucose, gelatin, acacia, sucrose, dextrin, guar gum, hydroxyethyl cellulose, polymethacrylates, maltodextrin, povidone, zein, methyl cellulose, and sodium alginate. It is well known that other compounds not listed can serve as binders and these compounds are not intentionally omitted herein.

Further the composition may include the mixture of the liquid, semi-liquid or crystalline decorporation agent with an additive in order to aid in the preparation of an acceptable pharmaceutical composition. For example, a liquid or semi-liquid decorporation agent may be added to a dry and porous pharmaceutical excipient such as colloidal silicon dioxide that absorbs the liquid in order to impart flow properties similar to the pharmaceutical excipient. Other examples of excipient include, but are not limited to, bentonite, cellulose, kaolin, and magnesium aluminum silicate. As another example, a crystalline decorporation agent may be added to dry pharmaceutical excipient to disperse the agent and improve flow. Examples of such excipients include, but are not limited to, lactose, mannitol, maltodextrin, and silicon dioxide.

Further the composition may include between about 0.01 and about 30 weight percent disintegrant. The disintegrant may be selected from a group consisting of alginic acid, crospovidone, croscarmellose sodium, soy polysaccharides, cellulose, magnesium aluminum silicate, povidone, sodium starch glycolate and sodium carboxymethyl starch. It is well known that other compounds not listed can have disintegrant properties and these compounds are not intentionally omitted herein.

In the following description there is shown and described preferred embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

DETAILED DESCRIPTION OF THE PREFERRED EMBODIMENTS OF THE INVENTION

Figure 1:
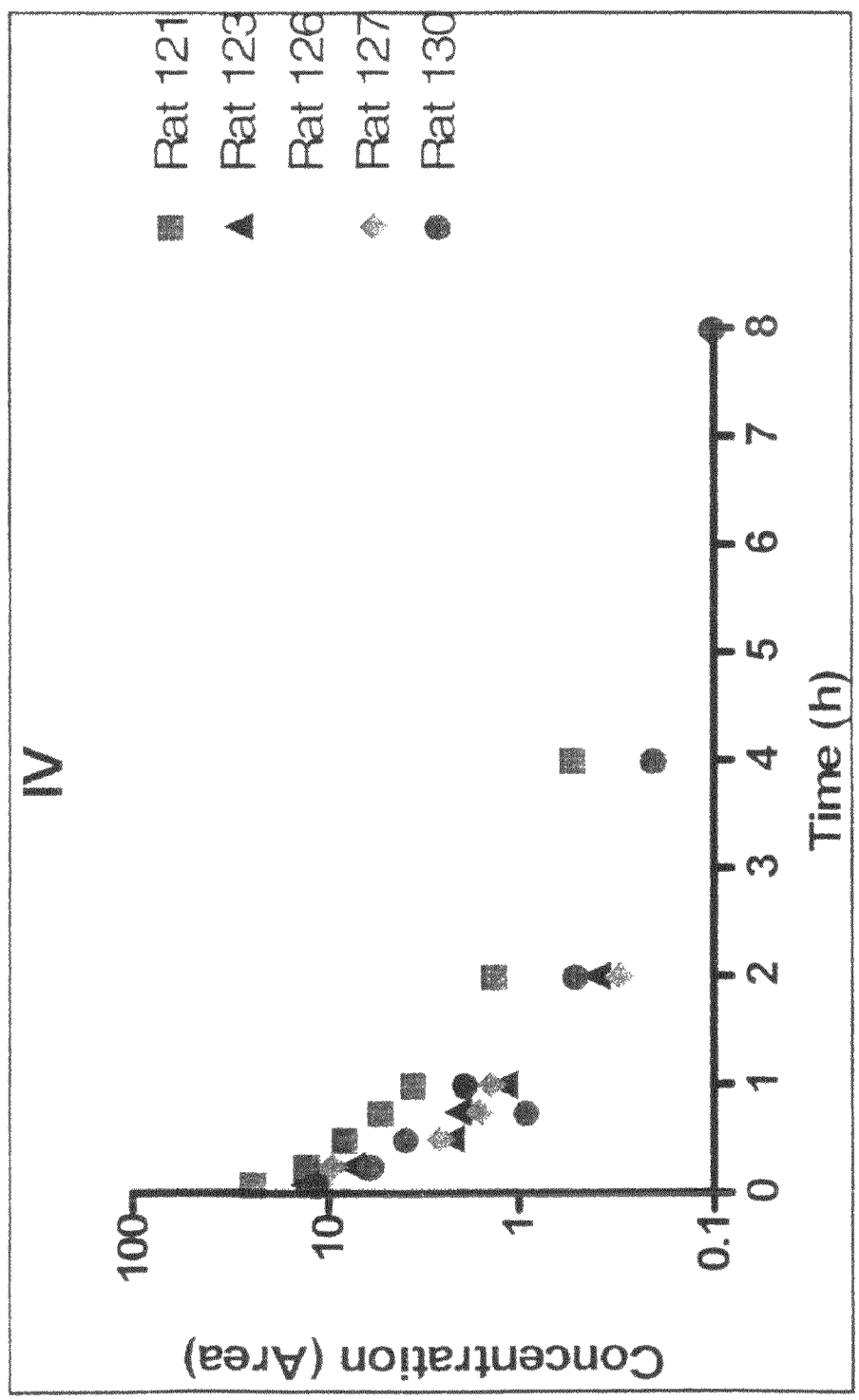
FIG. 1 graphically illustrates the bio-availability of 5 mg of DTPA administered to rats intravenously.

A composition for removing radioactive elements and compounds, such as transuranic compounds, from a mammal, such as a human, comprises a pharmaceutical carrier and a pharmaceutically effective amount of a decorporation agent having a chemical formula

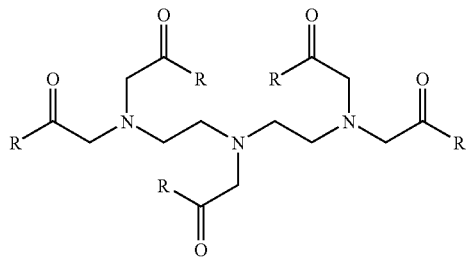

where R=—OR$^1$ or —NHR$^2$;

R$^1$=same or different and is independently selected from H, C$_1$-C$_{30}$ alkyl, C$_2$-C$_{30}$ alkenyl, C$_2$-C$_{30}$ alkynyl or benzyl and at least one R$^1$ is not hydrogen; and R$^2$=same or different and is independently selected from C$_1$-C$_{30}$ alkyl, C$_2$-C$_{30}$ alkenyl, C$_2$-C$_{30}$ alkynyl, benzyl or phenylalanine ethyl ester.

The phrase "pharmaceutical carrier" as used herein means a pharmaceutically-acceptable material, composition or vehicle, such as a liquid or solid filler, diluent, excipient, solvent or encapsulating material, involved in carrying and transporting an active agent, in this case the decorporation agent, from one organ or portion of a subjects body to another organ, or portion of the subjects body. Some examples of materials that can serve as pharmaceutical carriers include: powdered cellulose, calcium carbonate, lactose, starch, polylactic acid, polyglycolic acid, phospholipids, mannitol, calcium sulfate, sorbitol, dicalcium phosphate, kaolin, sodium chloride, powdered sugar and microcrystalline cellulose.

The phrase "pharmaceutically effective amount" as used herein means that amount of decorporation agent which is effective for removing systemic transuranic compounds from a mammal or for producing some other desired therapeutic effect in a mammal in accordance with a reasonable benefit/risk ratio applicable to any medical treatment.

The phrase "medically sufficient decorporation" relates to the administration of the decorporation agent to a mammal to result in detectable elimination of the radioactive element and/or compound from the mammal in the urine, feces, other bodily fluids and exhaled gas from the lungs. It is appreciated by those in the field that the transuranic compounds are very poisonous and radiotoxic in the body. A decorporation agent that when administered over time removes detectable amount of the transuranic compound from the body will generally improve the medical condition of the mammal. Thus, it is envisioned that dosing of the decorporation agent should continue until the transuranic compound is no longer detectable by the various modes of elimination from the body.

Antioxidants useful in the present invention include but are not limited to ascorbic acid, its salts and esters; fumaric acid, its salts and esters; malic acid, its salt and esters; alpha-tocopherol, its salts and esters; sodium metabisulphite, sodium bisulfite; butylated hydroxyanisole (BHA); butylated hydroxytoluene (BHT); gallic acid, its salts and esters; EDTA.

Preservatives useful in the present invention include but are not limited to methylparaben, ethylparaben, propylparaben, butylparaben, benzoic acid, sodium benzoate, benzyl alcohol, sorbic acid and potassium sorbate, EDTA, glycerol, phenol, thimerosol, phenoxyethanol, and cresol.

Binders useful in the present invention include but are not limited to microcrystalline cellulose, dibasic calcium phosphate, starch, glucose, gelatin, acacia, sucrose, dextrin, guar gum, hydroxyethyl cellulose, polymethacrylates, maltodextrin, povidone, zein, methyl cellulose, and sodium alginate.

Possible formulations include those suitable for oral, sublingual, buccal, nasal, pulmonary, rectal, and topical administration. Most suitable means for administration for a particular patient will depend on the nature and severity of the transuranic poisoning, the length of time between the poisoning and the discovery of the poisoning and, obviously, the age and condition of the patient.

Formulations suitable for oral administration may be provided as discreet units, such as tablets, capsules, chewing gum, lozenges or the like, which containing a predetermined amount of the decorporation agent: as powders or granules, as solutions or suspensions in aqueous or non-aqueous liquids, or as oil-in-water or water-in-oil emulsions, or as micelles, nanoparticles, liposomes, or microparticles. For example, the formulation may include a viscosity-enhancing agent such as beeswax, other waxes, polymer, glycerolmonooleate, lecithin, PEG 400 Monostearate, hydroxy propyl cellulose, hydroxy propyl methyl cellulose, polyethylene glycol 8000 (PEG 8000), PEG 3350, methyl cellulose, 2-propenoic acid (Carbopol 934P), polysorbate 20 (Tween 20), polysorbate 80 (Tween 80) and alpha-Tocopheryl polyethylene glycol 1000 succinate (TPGS) and mixtures thereof. The formulation is heated and then filled into hard gelatin capsules. Upon cooling, the capsules would contain a semi-solid material that included the decorporation agent.

Formulations suitable for sub-lingual or bucal administration include lozenges, rapidly dissolving tablets, thin-films, lollipops comprising the decorporation agent and, typically a flavored base, such as sugar and acacia or tragacanth in pastilles comprising the active compound in an inert base, such as gelatin and glycerin or sucrose acacia.

Formulations particularly useful for pediatric administration include oil solutions and self-emulsifying drug delivery systems. A simple oil-based solution contains dissolved decorporation agent. Various oils may be utilized including pharmaceutical grade vegetable oils such as (1) long-chain triglycerides such as corn oil, cottonseed oil, sesame oil and soybean oil and (2) medium-chain triglycerides such as mineral oil.

Self-emulsifying drug delivery systems are mixtures of oils, surfactants and solvents that can improve the oral absorption of highly lipophilic compounds. They can be formulated as microemulsion pre-concentrates that will spontaneously self-emulsify upon ingestion after dilution by the aqueous fluids of the GI tract. Unlike a non-emulsion formulation that relies on endogenous surfactants (i.e. bile salts) for emulsification, self-emulsifying drug delivery systems contain exogenous surfactants to self-promote micelle formation. The emulsification increases the surface area of the solubilized phase of the drug, thereby increasing absorption potential.

Formulations of the invention may be prepared by any suitable method, typically by uniformly and intimately admixing the decorporation agent and carrier in the required proportions and then, if necessary shaping the resulting mixture into the desired shape. For example, a tablet may be prepared by compressing an intimate mixture comprising a powder or granules of the decorporation agent and one or more optional ingredients such as a binder, lubricant, inert dilutant or surface active dispersing agent, or by molding an intimate mixture of powdered decorporation agent and inert liquid dilutant. In addition, a solution or suspension of the decorporation agent may be filled into a solid dose form such as a hard-gelatin capsule or soft-gelatin capsule.

In addition to the ingredients mentioned above, formulations to the present invention may include other additives known to those skilled in the art of pharmacy to be useful for their intended purpose. For example, formulations suitable for oral administration may include flavoring agents.

The method of treating a mammal to remove radioactive elements or compounds such as systemic transuramic compounds may be broadly described as comprising administering to the mammal a pharmaceutically effective amount of a decorporation agent having a chemical formula

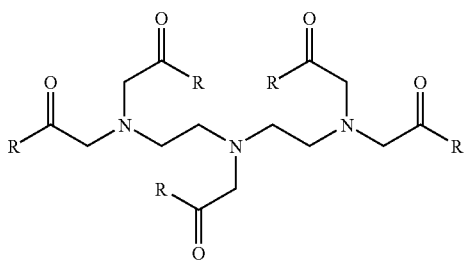

where R=—OR$^1$ or —NHR$^2$;
R$^1$=same or different and is independently selected from H, C$_1$-C$_{30}$ alkyl, C$_2$-C$_{30}$ alkenyl, C$_2$-C$_{30}$ alkynyl or benzyl and at least one R$^1$ is not hydrogen; and
R$^2$=same or different and is independently selected from C$_1$-C$_{30}$ alkyl, C$_2$-C$_{30}$ alkenyl, C$_2$-C$_{30}$ alkynyl, benzyl or phenylalanine ethyl ester.

Alternatively, the method may be described as comprising administrating to the mammal a pharmaceutically effective dosage amount of a pharmaceutical composition including a pharmaceutical excipient and a decorporation agent having a chemical formula

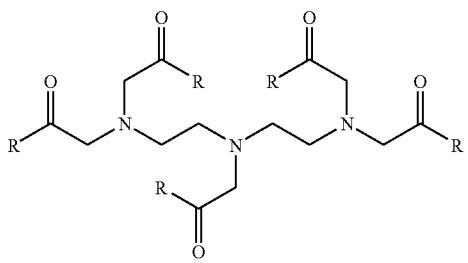

where R=—OR$^1$ or —NHR$^2$;
R$^1$=same or different and is independently selected from H, C$_1$-C$_{30}$ alkyl, C$_2$-C$_{30}$ alkenyl, C$_2$-C$_{30}$ alkynyl or benzyl and at least one R$^1$ is not hydrogen; and
R$^2$=same or different and is independently selected from C$_1$-C$_{30}$ alkyl, C$_2$-C$_{30}$ alkenyl, C$_2$-C$_{30}$ alkynyl, benzyl or phenylalanine ethyl ester. Either oral or nasal administration may be utilized.

The method includes administering between about 5 and about 250 milligrams and more typically between about 15 and about 45 milligrams of decorporation, agent per kilogram of the mammal's total body weight per day. Further the method includes administering the decorporation agent for at least one day and, if needed, over an extended period of time such as over days and weeks.

The following synthesis and examples are presented to further illustrate the invention, but it is not to be considered as limited thereto. The nomenclature system for the substituted DTPA compounds is as follows:

| Abbreviation | Compound |
|---|---|
| C2E5 | ethyl ester, penta-substituted |
| C12E5 | lauryl ester, penta-substituted |
| C18E5 | stearyl ester, penta-substituted |
| C$_{benzyl}$E5 | benzyl ester, penta-substituted |
| C$_{pheer}$A5 | amide of phenylalanine ethyl ester, penta-substituted |

Prodrug Synthesis

Target molecules preparation summary: DTPA esters may be prepared using DTPA as a starting material. The starting material diethylenetriaminepentaacetic acid, (DTPT, 1) could be smoothly converted to the pentaethyl ester 2, (C2E5) in high yield by refluxing the pentaacid in ethanol acidified with HCl gas, aqueous HCl, sulfuric acid, etc, etc. Removal of the solvent yielded the hydrochloride salt of:

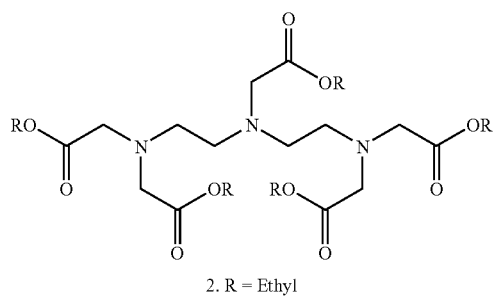

2. R = Ethyl as a glassy, hygroscopic solid. We also prepared the free base as a clear, colorless oil by washing with an aqueous sodium carbonate solution, drying the organic layer with sodium sulfate and removal of the volatiles. The corresponding C$_{18}$ pentaester:

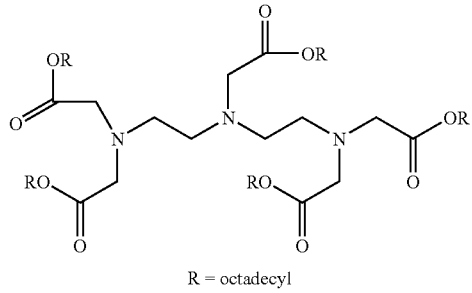

R = octadecyl was prepared by heating DTPA in toluene in an excess of 1-pentadecanol in the presence of sulfuric acid with azeotropic removal of water. Column chromatography to remove the excess alcohol provided the above compound as a waxy solid. We prepared the C$_{12}$ pentaester:

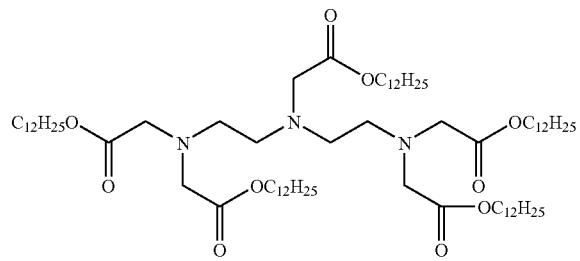

by a different route. Dodecylbromo acetate was prepared cleanly from 1-dodecanol and bromo acetyl bromide. The bromoacetate was reacted with diethylenetriamine to yield, after column chromatography, the C12E5 as an orange oil.

DTPA Derivatization

Attention was next turned to the preparation of DTPA esters by the alternate pathway shown in Scheme 2. The carbon skeleton of DTPA can be prepared by reaction of bromoacetic acid derivatives. The pentadodecyl ester C12E5 was prepared by reaction of dodecylbromoacetate 7 with diethylenetriamine to produce the requisite pentaester which was purified by column chromatography.

The triester series was approached by first reacting diethylenetriamine with ethyl trifluoroacetate in dichloromethane to produce the ditrifluoroacetamide 9 in good yield. Further reaction with 3 equivalents of ethyl bromoacetate and a base provided the triethyl ester 10, and using 1 equivalent of ethyl bromoacetate, the monoester 11.

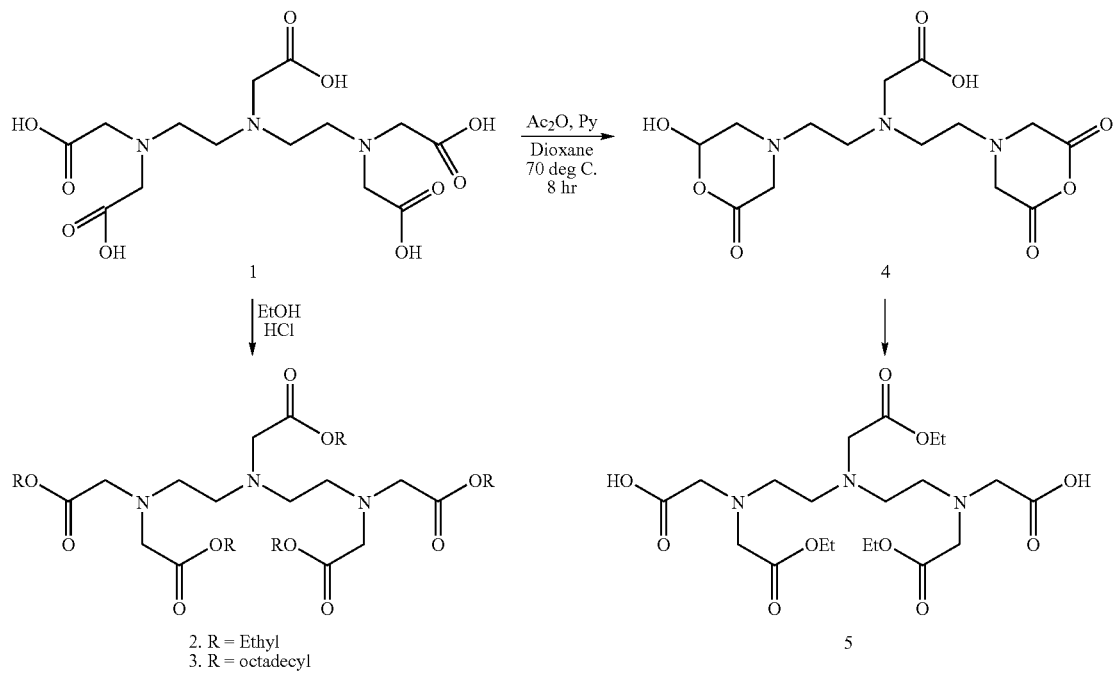

Scheme 1. DTPA Ester via DTPA derivatization

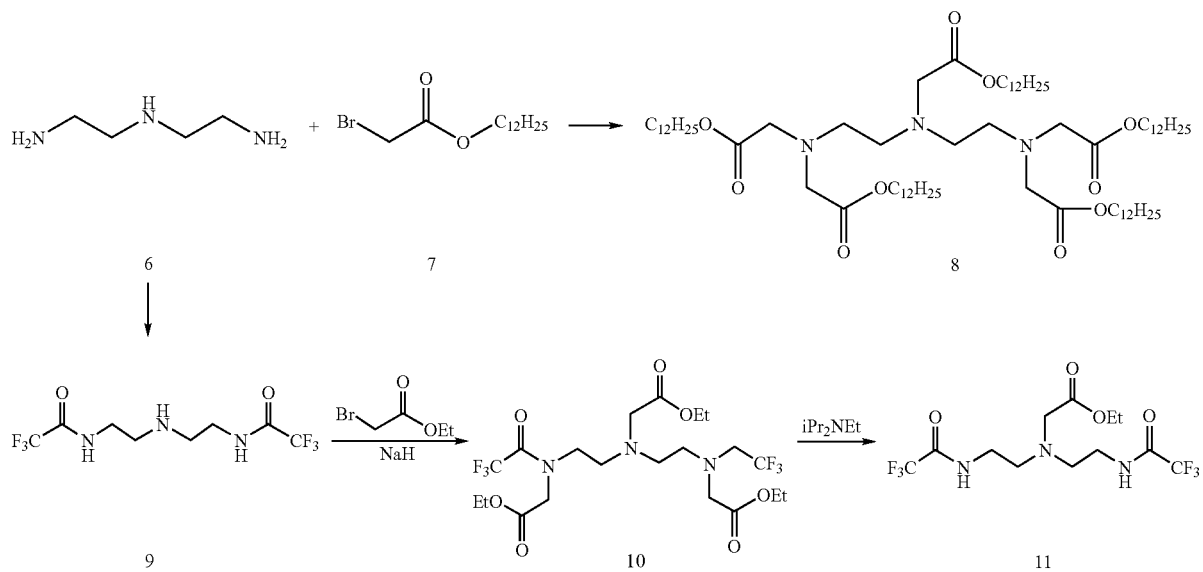

Scheme 2. DTPA Ester Synthesis

EXPERIMENTAL EXAMPLES

DTPA Pentaethyl Ester (C2E5), 2

DTPA (5 g, 12.7 mmol) was suspended in anhydrous absolute ethanol (200 mL) that had been saturated with anhydrous HCl. The reaction was stirred at reflux overnight under an Argon atmosphere. Approximately 20 mL of ethanol was distilled, and the reaction kept at reflux a further 24 h. The volatiles were removed in vacuo and a glassy, hygroscopic solid was obtained in quantitative yield (7.2 g). To prepare the free base, the material was dissolved in dichloromethane and washed with 5% aqueous potassium carbonate, dried with $Na_2SO_4$ and concentrated in vacuo to yield a clear, colorless oil. Mass spectrum (M+1) EI, 534. $^1$H-NMR ($CDCl_3$) 4.16 (q, J=7 Hz, 10H); 3.58, (s, 8H), 3.48, (s, 2H), 2.86-2.80 (complex multiplet, 8H), 1.27 (t, J=7 Hz, 12H), 1.26 (t J=7 Hz, 3H).

DTPA Penta $C_{18}$ Ester (C18E5), 2

DTPA (5.0 g, 12.7 mmol) was suspended in toluene and 3 mL concentrated sulfuric acid added. Octadecyl alcohol (31 g, 114 mmol) was added and the reaction fitted with a Dean-Stark apparatus. The reaction was refluxed overnight whereupon the volatiles removed. The crude material was dissolved in dichloromethane and separated by column chromatography (silica gel) eluting with dichloromethane and then 20% methanol in dichloromethane to yield 2 (15.2 g) as an off-white waxy solid.

DTPA Bis-Anhydride, 3.

DTPA (50 g, 0.13 mol) was added to freshly distilled acetic anhydride (80 mL) and anhydrous pyridine (80 mL) and anhydrous dioxane (50 mL), and heated to 70° C. under an Ar atmosphere for 7 h. The reaction was cooled, filtered, and the solid dried under high vacuum at 50° C. to yield the bisanhydride 3 (35 g) as an off-white powder. Mp 183-186. $^1$H-NMR (DMSO-$d_6$) 13.5 (bs, 1H), 3.66 (s, 2H), 3.45 (s, 8H), 3.07 (t, J=6.0 Hz, 4H), 2.92 (t, J=6.0 Hz, 4H).

Pentadodecyl Ester of DTPA (C12E5), 8.

To a solution of 1-dodecanol (25.0 g, 0.134 mol) in dichloromethane (150 mL), triethylamine (21.0 mL, 0.150 mol) and dimethylaminopyridine (0.5 g) was added a solution of bromoacetyl bromide (27.6 g, 0.137 mol) in dichloromethane (50 mL) at 5° C. dropwise. The mixture was stirred to room temperature overnight. The mixture was filtered, washed with brine and dried over $MgSO_4$ and the volatiles removed. The product dodecyl ester was used without further purification. Diethylenetriamine (2.52 g, 0.0244 mol) was dissolved in anhydrous acetonitrile (250 mL) and diisopropylethylamine (21.1 g, 0.742 mol) added. A solution of bromoester 7 (50.0 g, 0.163 mol) in acetonitrile (100 mL) was added slowly keeping the internal temperature below 15° C. The reaction was then allowed to stir to room temperature overnight. The volatiles were removed and the residue dissolved in ethyl acetate and washed with saturated sodium bicarbonate, dried over $Na_2SO_4$ and the solvent removed to an orange oil. Chromatography on silica gel (5% methanol-chloroform) yielded an orange oil. MS (MALDI), 1235 (M+1).

Ditrifluoroacetamide 9.

A solution of diethylenetriamine (20.0 g, 0.194 mol) in dichloromethane (500 mL) was cooled to 0° C. and ethyltrifluoroacetate added dropwise. The reaction was stirred to room temperature overnight and then the solvent and volatiles removed in vacuo to provide a white solid. MS (EI) 296 (M+1).

Triethyl ester (C2E3), 10.

The above ditrifluoroacetamide 9 (55 g, 0.186 mol) was dissolved in anhydrous DMF (200 mL) and added slowly at 0° C. to a solution of NaH (15.6 g, 0.650 mol) in DMF (200 mL). The reaction was allowed to stir 2 h then bromoethylacetate (99.0 g, 0.595 mol) added, and the reaction warmed to room temperature overnight. The reaction was diluted with aqueous sodium bicarbonate, and extracted with ethyl acetate, which was back extracted with brine. The organic layer was dried, and the volatiles removed to produce an oily glass. MS (MALDI) 554 (M+1).

Monoethyl Ester 11.

The di-trifluoroacetamide 9 (55 g, 0.186 mol) was dissolved in anhydrous acetonitrile (300 mL), and diisopropylethylamine (28.9 g, 0.223 mol) added. Ethylbromoacetate (37.4 g, 0.223 mol) was added dropwise to the solution and then it was stirred overnight at room temperature. The reaction was diluted with aqueous sodium bicarbonate, and extracted with ethyl acetate, which was back extracted with brine. The organic layer was dried, and the volatiles removed to produce an oily glass. MS (MALDI) 382 (M+1).

Prodrug Synthesis

Various esters of DTPA were prepared from diethylenetriamine, 6. The primary amines could be selectively protected as the di-trifluoroacetamide by reaction with ethyl trifluoroacetate to produce 9 in good yield. Reaction of 9 with 3 equivalents of ethylbromoacetate and NaH produced the triester 10. Reaction of 9 with 1 equivalent of ethylbromoacetate produced the monoester 11.

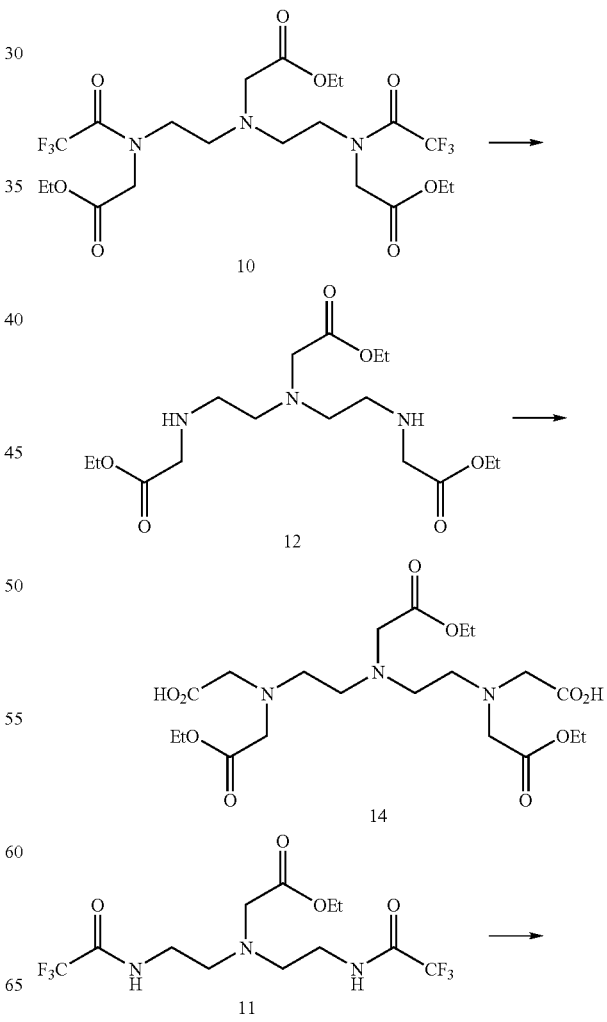

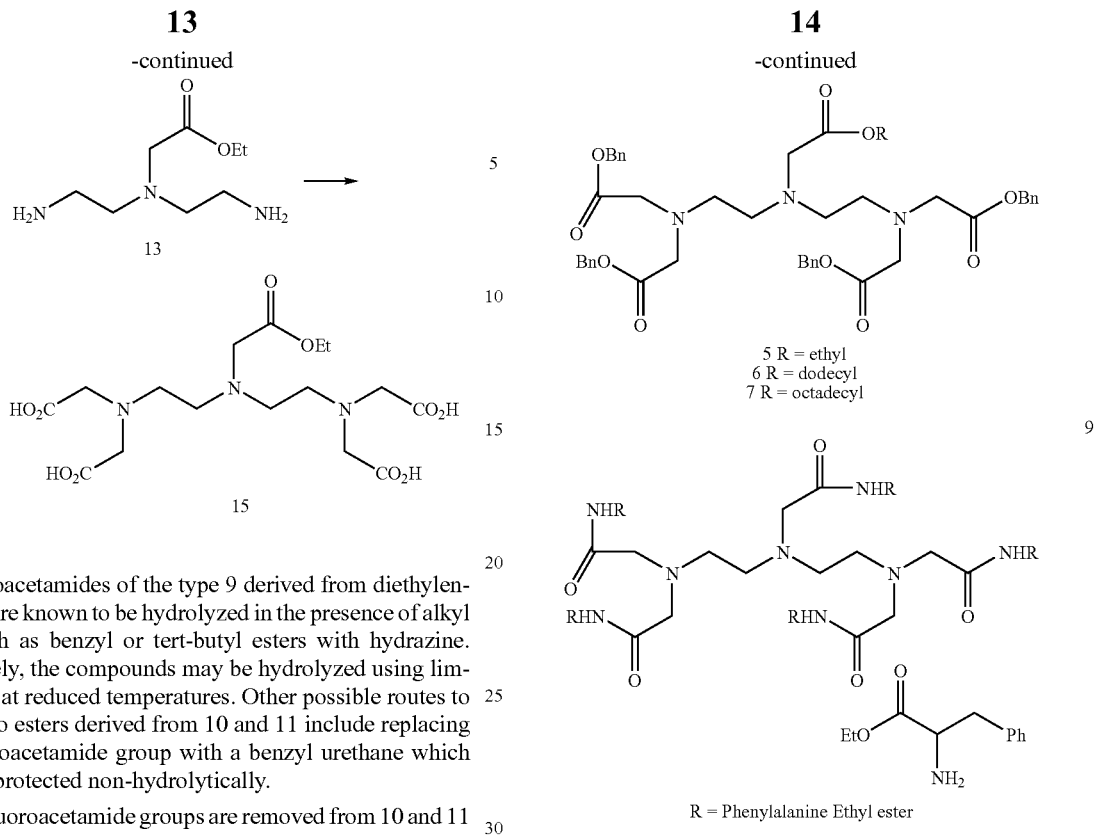

Trifluoroacetamides of the type 9 derived from diethylenetriamine are known to be hydrolyzed in the presence of alkyl esters, such as benzyl or tert-butyl esters with hydrazine. Alternatively, the compounds may be hydrolyzed using limiting KOH at reduced temperatures. Other possible routes to the diamino esters derived from 10 and 11 include replacing the trifluoroacetamide group with a benzyl urethane which can be de-protected non-hydrolytically.

The trifluoroacetamide groups are removed from 10 and 11 to produce the mono-ethyl and the tri-ethylacetate esters of diethylenetriamine, 12 and 13. Compounds 12 and 13 my be alkylated. The $C_{12}$ and $C_{18}$ analogs of 12 and 13 are prepared by the analogous routes. From these, C12E1, C12E3, C18E1, and C18E3 are prepared.

In yet another alternative scheme the trifluoroacetamides 10, 11 may be hydrolyzed using a limiting amount of hydroxide at reduced temperatures.

Preparation of the Pentabenzylester 8 and the Pentaamide 9

The pentabenzyl ester 8, $C_{benzyl}E5$ was prepared as the free base. The viscous oil was readily prepared and purified by column chromatography in multi-gram scale. The pentaamide 9, based upon the natural enantiomer of phenylalanine, was prepared from phenylalanine ethyl ester in good yield as a white powder.

Prodrug Synthesis

Chemical Synthesis

Two new prodrugs were synthesized and purified. The chemical characterization of these compounds confirmed their structure.

The synthesis of the $^{14}C$-labeled analog of one of these prodrugs, C2E5, was completed and its radiochemical purity was confirmed. A portion of the product was de-esterified to yield $^{14}C$-DTPA. Both $^{14}C$-C2E5 and $^{14}C$-DTPA were used in an animal study.

Schematic of Reaction Pathway for:

DTPA Triethyl Ester.

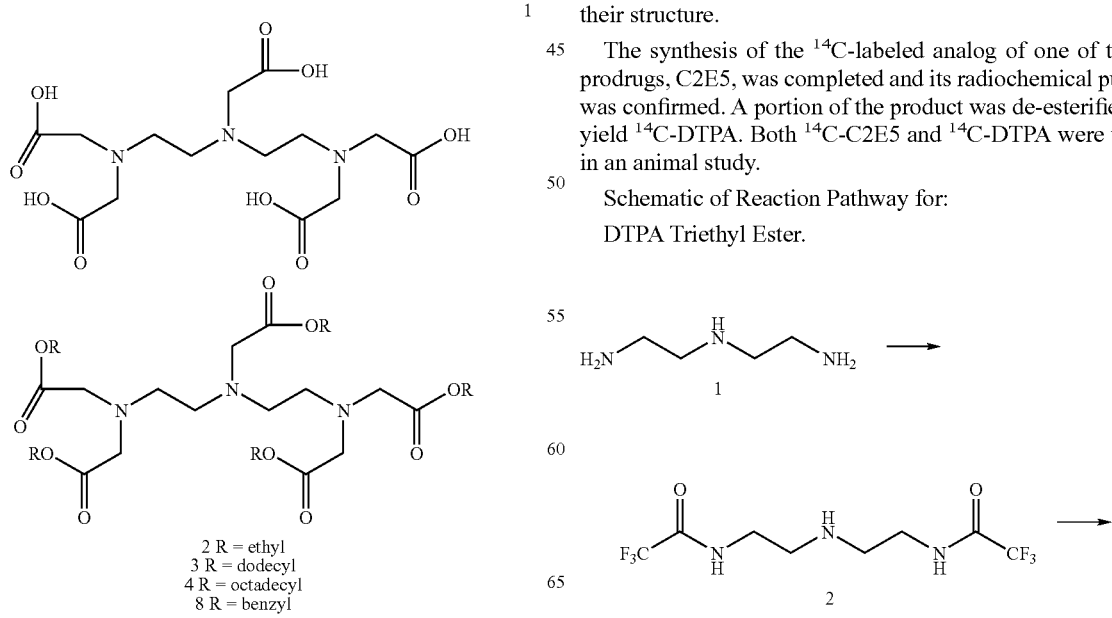

-continued

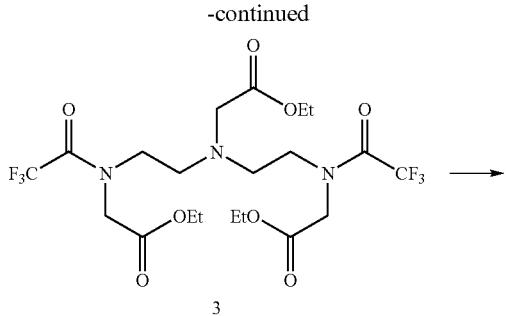

3

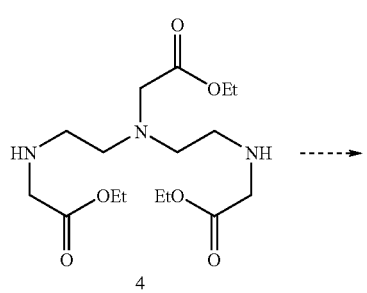

4

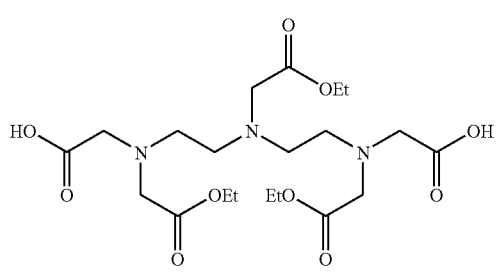

5

Using similar technology, the penta-dodecyl DTPA ester has been prepared.

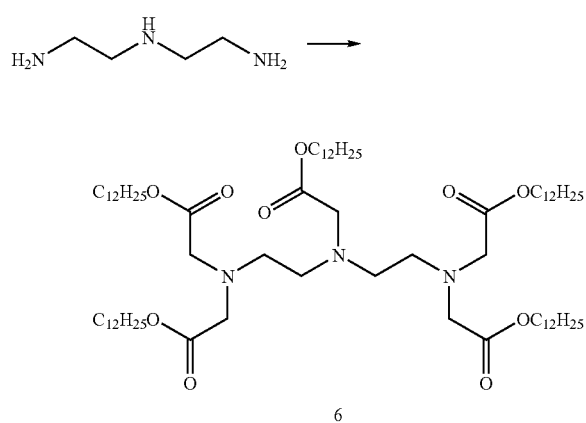

6

Oral Solution Formulations as Examples of Pharmaceutical Compositions

Two oral solution formulations were developed. The first formulation was alcohol free while the second formulation contained a 10% ethanol to maximize the solubility of the decorporation agent. The composition of the oral solution formulations is as follows:

| C2E5 Oral Solution Formulation 1 | | |
|---|---|---|
| Ingredient | Concentration | Function |
| C2E5 base | 75 mg/mL | Active |
| Citric acid | 2.10% w/v | Buffer/Solubilizing agent |
| Methyl paraben | 0.18% w/v | Preservative (Ideal for the pH range 4-8) |
| Propyl paraben | 0.02% w/v | Preservative (Ideal for the pH range 4-8) |
| Propylene glycol | 3.00% w/v | Cosolvent, Preservative aid |
| Sorbitol | 10.00% w/v | Sweetening agent |
| Disodium EDTA | 0.10% w/v | Anti-oxidant |
| Purified water | q.s. to 100 mL | Vehicle |

| C2E5 Oral Solution Formulation 2 | | |
|---|---|---|
| Ingredient | Concentration | Function |
| C2E5 base | 75 mg/mL | Active |
| Citric acid | 2.10% w/v | Buffer/Solubilizing agent |
| Methyl paraben | 0.18% w/v | Preservative (Ideal for the pH range 4-8) |
| Propyl paraben | 0.02% w/v | Preservative (Ideal for the pH range 4-8) |
| Propylene glycol | 3.00% w/v | Cosolvent, Preservative aid |
| Sorbitol | 10.00% w/v | Sweetening agent |
| Disodium EDTA | 0.10% w/v | Anti-oxidant |
| Ethanol | 10.0% w/v | Co-solvent |
| Purified water | q.s. to 100 mL | Vehicle |

Bioavailability Study

Figure 2:
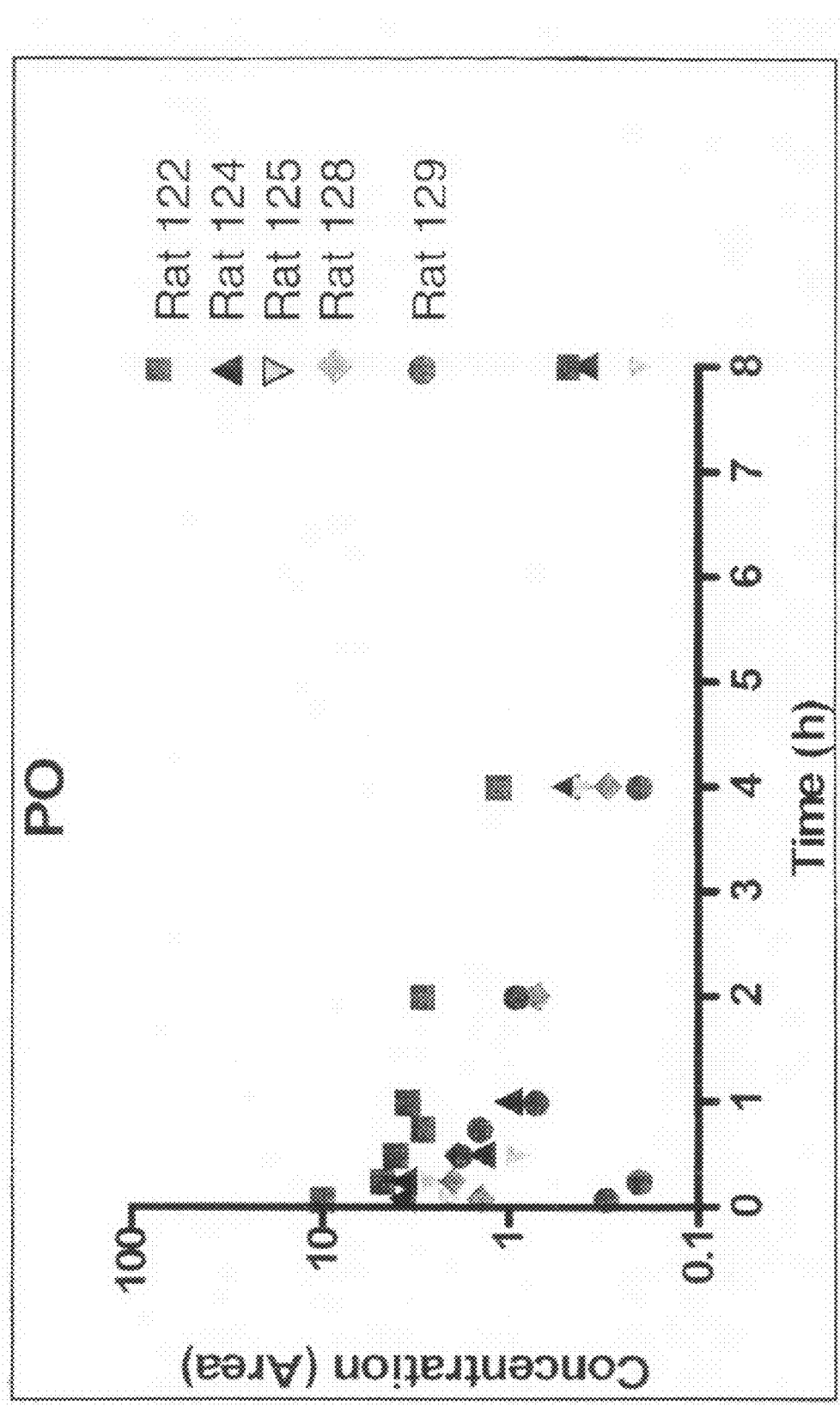
FIG. 2 graphically illustrates the bioavailability of an equivalent molar dose of decorporation agent of the present invention orally administered to a rat in a 10% ethanol solution.

A bioavailability study was conducted in which five rats were intravenously administered 5 mg of DTPA and another 5 rats were orally administered an equivalent lower dose (approximately 7 mg) of C2E5 in a 10% ethanol solution. Blood samples were obtained at regular intervals from an in-dwelling catheter that had been surgically implanted prior to the administration of the doses. The pharmacokinetic analysis of the data is presented in FIGS. 1 and 2.

The data indicates that the bioavailability of C2E5 is essentially 100% in the rat model. Since no C2E5 can be detected in the plasma, it appears that once C2E5 is absorbed from the gastrointestinal tract it is quantitatively and rapidly converted to DTPA. As expected the blood concentration profile results in lower blood levels and a longer duration compared to IV DTPA.

Small Animal Decorporation Efficacy Study

Studies in small groups of animals have demonstrated that the decorporation of $^{241}$Am following oral administration of C2E5 to rats compared favorably to decorporation following IV administration of equivalent doses of DTPA.

The invention has been described herein with regard to certain preferred pharmaceutical composition embodiments and treatment methods. However, as obvious variations thereon become apparent to those skilled in the art, the invention is not to be considered as limited thereto.

What is claimed:

1. A method of treating a mammal to remove a radioactive element or compound, comprising:
   administering to said mammal a pharmaceutically effective amount of a decorporation agent having a chemical formula:

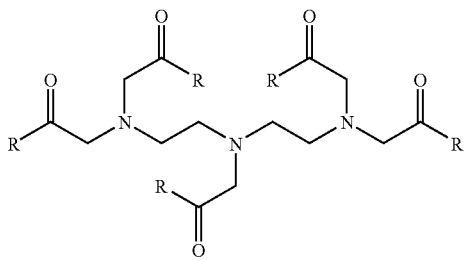

where R=—$OR^1$ or —$NHR^2$;
$R^1$=same or different and is independently selected from H, $C_1$-$C_{30}$ alkyl, $C_2$-$C_{30}$ alkenyl, $C_2$-$C_{30}$ alkynyl or benzyl and at least one $R^1$ is not hydrogen; and
$R^2$=same or different and is independently selected from $C_1$-$C_{30}$ alkyl, $C_2$-$C_{30}$ alkenyl, $C_2$-$C_{30}$ alkynyl, benzyl or phenylalanine ethyl ester.

2. The method of claim 1, including using oral administration.

3. The method of claim 1, including administering between about 5 and about 250 milligrams of decorporation agent per kilogram of said mammal's total body weight per day.

4. The method of claim 3, including administering said decorporation agent for at least an extended period of time such as over days and weeks in order to achieve medically sufficient decorporation.

5. A method of treating a mammal to remove a radioactive element or compound, comprising:
   administering to said mammal a pharmaceutically effective amount of a pharmaceutical composition including a pharmaceutical carrier and a decorporation agent having a chemical formula:

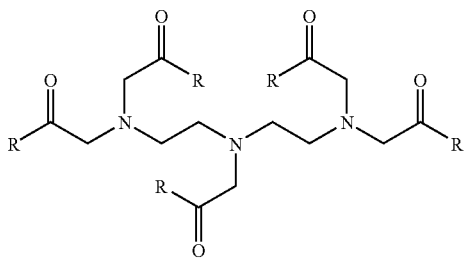

where R=—$OR^1$ or —$NHR^2$;
$R^1$=same or different and is independently selected from H, $C_1$-$C_{30}$ alkyl, $C_2$-$C_{30}$ alkenyl, $C_2$-$C_{30}$ alkynyl or benzyl and at least one $R^1$ is not hydrogen; and
$R^2$=same or different and is independently selected from $C_1$-$C_{30}$ alkyl, $C_2$-$C_{30}$ alkenyl, $C_2$-$C_{30}$ alkynyl, benzyl or phenylalanine ethyl ester.

6. The method of claim 5, wherein said pharmaceutical composition also includes an antioxidant.

7. The method of claim 5, wherein said pharmaceutical composition also includes a preservative.

8. The method of claim 5, wherein said pharmaceutical composition also includes a binder.

9. The method of claim 5, including using oral administration.

10. The method of claim 5 including administering between about 15 and about 45 milligrams of decorporation agent per kilogram of said mammal's total body weight per day.

11. The method of claim 5, including administering said decorporation agent for at least an extended period of time such as over days and weeks in order to achieve medically sufficient decorporation.

12. A composition for removing a radioactive element or compound from a mammal, comprising:
    a pharmaceutical carrier; and
    a pharmaceutically effective amount of a decorporation agent having a chemical formula:

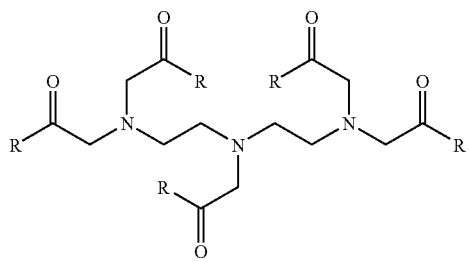

where R=—$OR^1$ or —$NHR^2$;
$R^1$=same or different and is independently selected from H, $C_1$-$C_{30}$ alkyl, $C_2$-$C_{30}$ alkenyl, $C_2$-$C_{30}$ alkynyl or benzyl and at least one $R^1$ is not hydrogen; and
$R^2$=same or different and is independently selected from $C_1$-$C_{30}$ alkyl, $C_2$-$C_{30}$ alkenyl, $C_2$-$C_{30}$ alkynyl, benzyl or phenylalanine ethyl ester.

13. The composition of claim 12, including between about 50 weight percent and about 98 weight percent carrier and the decorporation agent in the carrier at a concentration ranging from 5 to 250 mg/mL.

14. The composition of claim 13 further including between about 0.001 and about 3 weight percent anti-oxidant.

15. The composition of claim 14, wherein said anti-oxidant is selected from a group consisting of ascorbic acid, its salts and esters; fumaric acid, its salts and esters; malic acid, its salt and esters; alpha-tocopherol, its salts and esters; sodium metabisulphite, sodium bisulfite; butylated hydroxyanisole (BHA); butylated hydroxytoluene (BHT); gallic acid, its salts and esters; EDTA.

16. The composition of claim 13, further including between about 0.001 and about 10 weight percent preservative.

17. The composition of claim 16, wherein said preservative is selected from a group consisting of methylparaben, ethylparaben, propylparaben, butylparaben, benzoic acid, sodium benzoate, benzyl alcohol, sorbic acid and potassium sorbate, EDTA, glycerol, phenol, thimerosol, phenoxyethanol, and cresol.

18. The composition of claim 13, further including between about 0.01 and about 25 weight percent binder.

19. The composition of claim 18, wherein said binder is selected from a group consisting of microcrystalline cellulose, silicon dioxide, dibasic calcium phosphate, starch, glucose, gelatin, acacia, sucrose, dextrin, guar gum, hydroxyethyl cellulose, polymethacrylates, maltodextrin, povidone, zein, methyl cellulose, and sodium alginate.

20. The composition of claim 13, further including between about 0.0001 and about 5.0 weight percent viscosity enhancer.

21. The composition of claim 20, wherein said viscosity enhancer is selected from a group consisting of beeswax, other waxes, polymer, glycerolmonooleate, lecithin, PEG 400 Monostearate, hydroxy propyl cellulose, hydroxy propyl methyl cellulose, polyethylene glycol 8000 (PEG 8000), PEG 3350, methyl cellulose, 2-propenoic acid (Carbopol 934P), polysorbate (Tween 20), polysorbate 80 (Tween 80) and alpha-Tocopheryl polyethylene glycol 1000 succinate (TPGS) and mixtures thereof.

* * * * *